United States Patent
Zhang et al.

(10) Patent No.: US 7,024,037 B2
(45) Date of Patent: Apr. 4, 2006

(54) CROSS-POLARIZED IMAGING METHOD FOR MEASURING SKIN ASHING

(75) Inventors: Xiaodong Zhang, Bloomfield, NJ (US); Liang Sheng Tsaur, Norwood, NJ (US); Helene Santanastasio, Pompton Plains, NJ (US); Pravin Shah, Rutherford, NJ (US); Srinivasan Krishnan, Union City, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 742 days.

(21) Appl. No.: 10/104,415

(22) Filed: Mar. 22, 2002

(65) Prior Publication Data
US 2003/0179929 A1 Sep. 25, 2003

(51) Int. Cl.
*G06K 9/00* (2006.01)

(52) U.S. Cl. .................. 382/181; 382/165; 382/275; 600/306; 600/340

(58) Field of Classification Search ............... 209/587; 250/225, 461.2; 348/77, 79; 356/71, 237.2, 356/303, 308, 326, 328, 342, 364, 369, 601; 382/118, 128, 154, 164, 165, 181, 190, 211, 382/275; 600/306, 310, 317, 340
See application file for complete search history.

(56) References Cited

U.S. PATENT DOCUMENTS

| | | | |
|---|---|---|---|
| 4,398,541 A * | 8/1983 | Pugliese | 600/476 |
| 4,412,246 A * | 10/1983 | Allen et al. | 348/79 |
| 5,005,975 A * | 4/1991 | Kawai et al. | 356/237.2 |
| 5,016,173 A * | 5/1991 | Kenet et al. | 382/128 |
| 5,028,138 A * | 7/1991 | Wolff | 356/369 |
| 5,101,101 A * | 3/1992 | Sawamura | 250/223 R |
| 5,198,875 A | 3/1993 | Bazin et al. | |
| 5,343,536 A | 8/1994 | Groh | |
| 5,669,868 A * | 9/1997 | Markoll | 600/14 |
| 5,742,392 A | 4/1998 | Anderson et al. | |
| 5,828,339 A * | 10/1998 | Patel | 343/700 MS |
| 5,828,451 A * | 10/1998 | Bellus et al. | 356/326 |
| 5,836,872 A * | 11/1998 | Kenet et al. | 600/306 |
| 5,986,746 A * | 11/1999 | Metz et al. | 356/71 |
| 6,032,071 A | 2/2000 | Binder | |
| 6,160,579 A * | 12/2000 | Shiraiwa et al. | 348/224.1 |
| 6,175,750 B1 * | 1/2001 | Cook et al. | 600/310 |
| 6,208,749 B1 * | 3/2001 | Gutkowicz-Krusin et al. | 382/128 |
| 6,215,893 B1 * | 4/2001 | Leshem et al. | 382/128 |
| 6,324,417 B1 * | 11/2001 | Cotton | 600/475 |
| 6,418,339 B1 * | 7/2002 | Essenpreis et al. | 600/476 |

(Continued)

FOREIGN PATENT DOCUMENTS

EP 1 167 950 A1 1/2002

(Continued)

OTHER PUBLICATIONS

Anderson RR., "Polarized light examination and Photography of th eskin", Jul. 1991, Arch Dermatol, 127 (7), 1000-5.*

(Continued)

*Primary Examiner*—Sanjiv Shah
*Assistant Examiner*—Gregory Desire
(74) *Attorney, Agent, or Firm*—Ronald A. Koatz

(57) ABSTRACT

A process for measuring skin ashing is provided. The process comprises selecting a desired skin testing area and acguiring an image of the area using x-polarization technique. The image is analyzed by obtaining a light distributing image, storing the difference between this image and the original image and using a differential in intensity to define ashing.

10 Claims, 2 Drawing Sheets

(a) original image (b) light distribution image (c) original image minus light distribution image (d) threshold image with white ashing area

U.S. PATENT DOCUMENTS

| | | | |
|---|---|---|---|
| 6,436,127 B1* | 8/2002 | Anderson et al. | 607/89 |
| 6,452,188 B1* | 9/2002 | Chubb | 250/372 |
| 6,587,711 B1* | 7/2003 | Alfano et al. | 600/476 |
| 6,740,868 B1* | 5/2004 | Knebel et al. | 250/234 |
| 6,907,193 B1* | 6/2005 | Kollias et al. | 396/4 |
| 6,949,115 B1* | 9/2005 | Mascio | 607/88 |
| 2003/0179929 A1* | 9/2003 | Zhang et al. | 382/181 |

FOREIGN PATENT DOCUMENTS

| | | |
|---|---|---|
| FR | 2 784 018 A | 4/2000 |
| GB | 2 147 421 A | 5/1985 |
| WO | 99/37980 | 7/1999 |

OTHER PUBLICATIONS

Paul Debevec et al., "Acquiring the Reflectance Field of a Human Face", SIGGRAPH 2000 Conference Proceedings, 145-156.*

S. L. Jacques et al., "Imaging skin with polarized light", Oct. 23-26, 2002, Proceedings of the Second Joint EMBS/BMES Conferencee, 2314-2315.* j. Philip et al., "Improved Optical Discrimination of Skin with Polorized Light", J. Soc. Cosmet. Chem., 39, 121-132 (1988).

*International Search Report* No. EP 0301660 dated Sep. 17, 2003—3 pages.

* cited by examiner

CROSS-POLARIZED IMAGING METHOD FOR MEASURING SKIN ASHING

FIELD OF THE INVENTION

The present invention relates to cross-polarized imaging methods which are used in a process for first acquiring a skin ashing image and then measuring the amount of skin ashing present.

BACKGROUND OF THE INVENTION

Ashing is a term often used by dark skin consumers to describe the dull, grayish appearance of their skin condition. Skin ashing is related to the overall white/grayish appearance of the skin caused by scattering of the uplifted corneocytes. The uplifted corneocytes that characterize ashing skin increase the diffuse scattering and reduce the reflection of light on the skin surface. As a result, the upper layers of stratum lose translucency and become opaque and dull.

The contrast of whiteness caused by the uplifted corneocytes on the skin surface can be greatly enhanced relative to darker skin by using a cross-polarized imaging technique. Specifically, this is done by suppressing the Fresnel Reflection contribution on the skin. Images obtained using a cross-polarized imaging method have been found very useful for quantifying skin ashing since the glare from Fresnel Reflection can severely influence the whiteness appearance of skin. By suppressing the Fresnel Reflection, the white ashing can therefore be seen more clearly.

Polarizers are used widely in photography to reduce glare. J. Philip (J. Soc. Cosmet. Chem., 39, 121, 1988), for example, discloses polarizers to reduce glare and get more sub-surface (e.g., viable epidermis and dermis in contrast to stratum corneum) information for images of skin. Philip used cross-polarization for improving optical discrimination of skin. However, Philip fails to teach or suggest use of cross-polarization as part of a process to measure skin ashing as described in the subject invention. More specifically, and as noted above, the technique he uses is for telangis (dermal) and age spots (viable dermis) rather than for measuring information on the stratum corneum such as is done in the subject invention where ashing is measured.

U.S. Pat. No. 5,198,875 to Bazin et al. describes a device that is designed to assess the brightness of a surface, more particularly of the skin. A device for measuring the brightness of the skin surface, using light-sensitive photo detectors at both parallel-polarized and cross-polarized conditions is described. Using this device, spectral brightness can be assessed by the parallel polarization results, and diffuse brightness can be assessed by the cross-polarized results. Therefore, Bazin et al. does not take an image of the skin and clearly fails to teach or suggest a method of measuring skin ashing.

No process for first acquiring an image and then using the image to quantify the amount of skin ashing is found in this or any prior art as far as applicants are aware.

Unexpectedly, applicants have now discovered that, using cross-polarized imaging, it is possible to quantify the degree of skin ashing.

BRIEF DESCRIPTION OF INVENTION

The present invention relates to the use of cross-polarized imaging methods for measuring the amount of skin ashing. In the embodiment of the present invention, skin ashing is measured (1) by choosing a desired spot on the subject's arms or legs (or any suitable spot on skin desired to be measured); (2) acquiring an image of said spot under cross-polarization (preferably, but not necessarily, a digital image); and (3) processing the captured images using an image processing program developed by the applicants to obtain skin in a defined area demonstrating "ashing" condition (e.g., with ashing above a defined threshold value).

More specifically, the invention comprises a cross-polarized imaging method for measuring skin shine comprising:
(1) Choosing a desired area on the body of a subject (generally the selected area is about 2 cm×2 cm);
(2) acquiring a cross-polarized digital image at 1 to 100 times magnification; and
(3) analyzing the captured images using an image analysis tool (e.g., program) to quantify the amount of skin ashing (see steps (a)–(d) of FIG. 1).

DETAILED DESCRIPTION OF INVENTION

The present invention relates to the use of cross-polarized imaging methods for measuring the amount of skin ashing. In one embodiment of the present invention, skin ashing is measured by choosing a desired spot on the subject's arms, legs or other desired area; acquiring an image of the desired area under cross-polarization (preferably, but not necessarily a digital image); and processing the captured images using an image processing program developed by the applicants to obtain a quantifiable measurement of said ashing.

More specifically, the invention comprises a cross-polarized imaging method for measuring skin ashing comprising:
(1) choosing a desired area on the body of a subject (generally the selected area is about 2 cm×2 cm, (although it may in theory be 0.5 to 100 cm$^2$);
(2) acquiring a cross-polarized image, preferably a digital image, at 1 to 100 times magnification (theoretically there is no limit to magnification); and
(3) analyzing the captured images using an image analysis tool in order to quantify the amount of skin ashing.

A typical test site is generally about 20 mm in diameter although it may range in size from 0.5 to 100 cm$^2$. A preferred magnification of the image is about 20 to 50 times. Cross-polarized images (e.g., digital photos) are obtained using an apparatus comprising a light source with a linear polarizer for projecting an incident beam of light on the skin surface and a camera with a second linear polarizer whose polarization direction is at about a right angle orientation of the polarization relative to the first polarizer. Small angle variations (e.g., 70–110°) may be tolerated although it is theoretically best at 90°.

For capturing images, any device capable of downloading images and projecting them to a screen or other area for viewing may be used. Preferably, the images are captured using, for example, a Sony FVP-1 Image Acquisition Unit or a computer with MGI PHOTOSUITE III SE or other software designed to download and project information.

Figure 1:
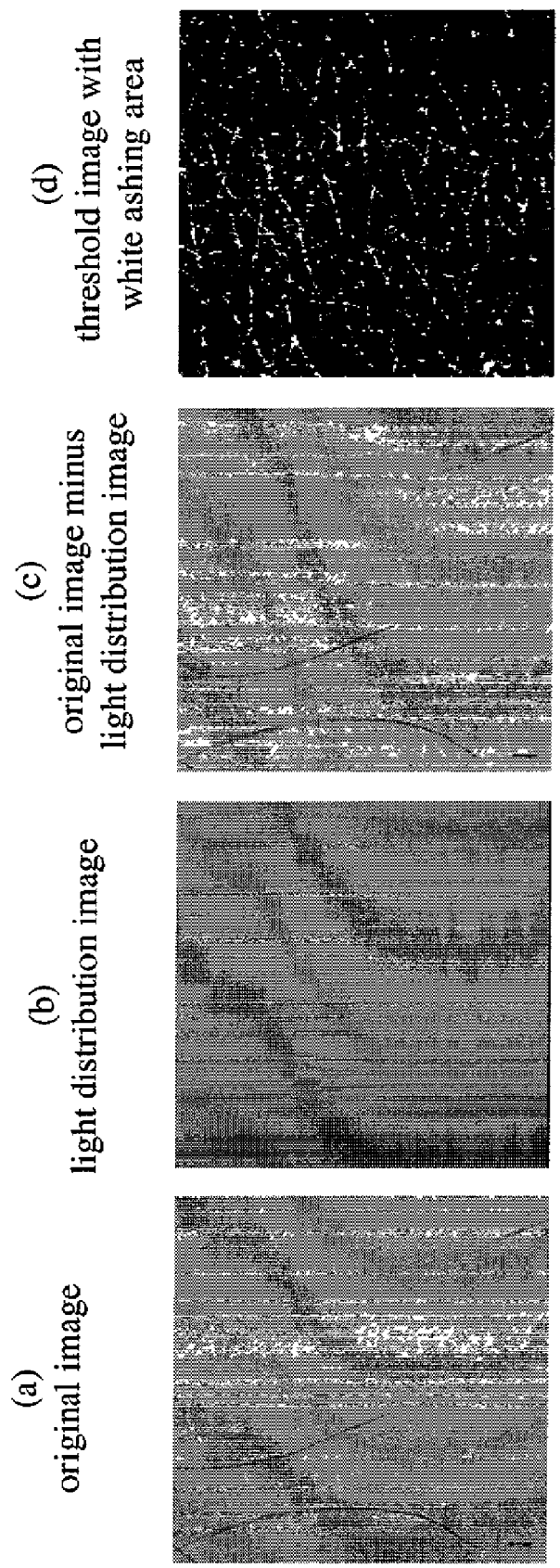
FIG. 1 shows a step by step analysis method from acquisition of an original image (a); to fitting the image to a parabola (b); to forming a new image (c) based on the difference in pixel intensity between parabolic fit and original image (defined as (a)–(b) and seen in (c)); to applying a fixed threshold over baseline intensity in order to form a black and white image representing percent of ashing (d).

The images are then analysed using a computer program by the following procedure:

1. This image (which may be in color or gray scale) is fitted by the program to a parabola in two dimensions (to obtain a light distribution image as seen in FIG. 1(b));
2. The difference between the light distribution image and the original image is then stored in a new image (see FIG. 1(c) in FIG. 1);
3. A fixed threshold over the baseline intensity is then applied to this image to reveal the areas that exhibit ashing. Applicants have arbitrarily defined the threshold as 20 intensity units over the baseline. However, it should be understood this intensity may be in a range of 2 to 100, preferably 5 to 50, more preferably 10 to 25 intensity units over the baseline.

In general "intensity units" are defined on a scale of 0 to 256 ($2^8$) where 0 is dark and 256 is bright. The baseline is calculated as the average intensity. Thus, areas which have, for example, 20 or more intensity units over the base meet threshold values for purposes of our definition. The amount of ashing over this threshold is defined as the % of ashing.

When this contrast is established, it is possible to readily ascertain these sights (where marked in white on the image seen in FIG. 1(d)) where ashing is truly occurring. The % of white marks in 1(d) as percentage of the total is the % ashing.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

METHODOLOGY

Equipment

A Charm View Video Microscope was used to capture cross-polarized skin images. It is a hand-held video camera with cross-polarization capacity which can effectively reduce surface reflection from the skin. A 30× magnification polarization lens was used. The field of view was approximately 7 mm by 9 mm. Images were captured under cross-polarized mode using Sony FVP-1 Image Acquisition Unit/Printer. Alternatively, the Charm View System can be connected to a laptop computer with proper image capturing software for image acquisition.

EXAMPLE 1

Skin Ashing Quantification

In this example, the quantification of skin ashing is demonstrated step by step as seen in FIG. 1. In step (a), the cross-polarized image is obtained. In step (b), a parabolic fit is done to fit the light intensity distribution in the image. The uneven light intensity distribution is caused by the lighting system and needs to be corrected. In step (c), the uneven light distribution (b) is corrected from the original image (a) by subtracting the pixel intensity of the parabolic fit from the pixel intensity of the original image. In step (d), pixels that stand 20 intensity units above the background are defined as ashing sites and are represented in white pixels. It should be understood that the intensity is arbitrarily defined, but we have used 20 as such arbitrary standard. The percentage of ashing in this example is calculated to be 4.17%. This means 4.17% of the pixels have an intensity of 20 units above the baseline (intensity units have range of 0 to 256 where 0 is dark and 256 is bright white). The baseline is calculated from the average intensity of the image. This process is referred to as thresholding. As noted, each of these steps is set forth in FIG. 1.

EXAMPLE 2

Visual Perception of Skin Ashing vs. Instrument Quantification Results

This example was conduced to show that observations of ashing as made by test subjects correlated with the ashing observations graded from cross-polarized images (FIG. 2(a)) as well as with % ashing results calculated (FIG. 2(b)).

Seven panelists participated in this ashiness pilot study.

Test Procedure:

1. Mark 2–4 sites (2 cm×2 cm) on panelist's arm that have different ashiness.
2. Ask 3–4 naïve subjects to grade the ashiness of each test site using the scale set forth in Table 1 below:

TABLE 1

| Level of Ash Intensity | |
|---|---|
| 0 | No ashing |
| 0.25 | Slight ashing |
| 0.50 | Moderate ashing |
| 0.75 | High ashing |
| 1.0 | Extreme ashing |

3. Take cross-polarized images of test sites using the Charm View camera.
4. Print out the cross-polarized images and ask four subjects to grade ashiness from the pictures (for FIG. 2(a)).
5. Analyze the cross-polarized images using the thresholding method defined in Example 1. Visual grading results direct from the test sites, visual grading results from cross-polarized images, and analysis from the thresholding analysis methods were tabulated in Table 2.

TABLE 2

Results of the skin ashing study.

| | Visual ashiness grade | Visual grade from cross-polarized pictures | % ashing area using image processing |
|---|---|---|---|
| Site 1 | 0.25 | 0.13 | 0.06 |
| Site 2 | 0.08 | 0.00 | 0.01 |
| Site 3 | 0.08 | 0.11 | 0.04 |
| Site 4 | 0.63 | 0.59 | 7.22 |

TABLE 2-continued

Results of the skin ashing study.

|  | Visual ashiness grade | Visual grade from cross-polarized pictures | % ashing area using image processing |
|---|---|---|---|
| Site 5 | 0.31 | 0.49 | 4.58 |
| Site 6 | 0.06 | 0.28 | 3.48 |
| Site 7 | 1.00 | 1.00 | 16.29 |
| Site 8 | 0.42 | 0.29 | 2.10 |
| Site 9 | 0.33 | 0.14 | 0.40 |
| Site 10 | 0.17 | 0.26 | 0.66 |
| Site 11 | 0.00 | 0.31 | 0.93 |
| Site 12 | 0.50 | 0.81 | 5.89 |
| Site 13 | 0.20 | 0.33 | 0.59 |
| Site 14 | 0.25 | 0.18 | 0.22 |
| Site 15 | 0.00 | 0.16 | 0.26 |
| Site 16 | 0.75 | 0.75 | 12.76 |
| Site 17 | 0.25 | 0.29 | 1.81 |
| Site 18 | 1.00 | 1.00 | 21.81 |
| Site 19 | 0.92 | 0.95 | 20.01 |
| Site 20 | 0.75 | 0.86 | 18.72 |

Figure 2:
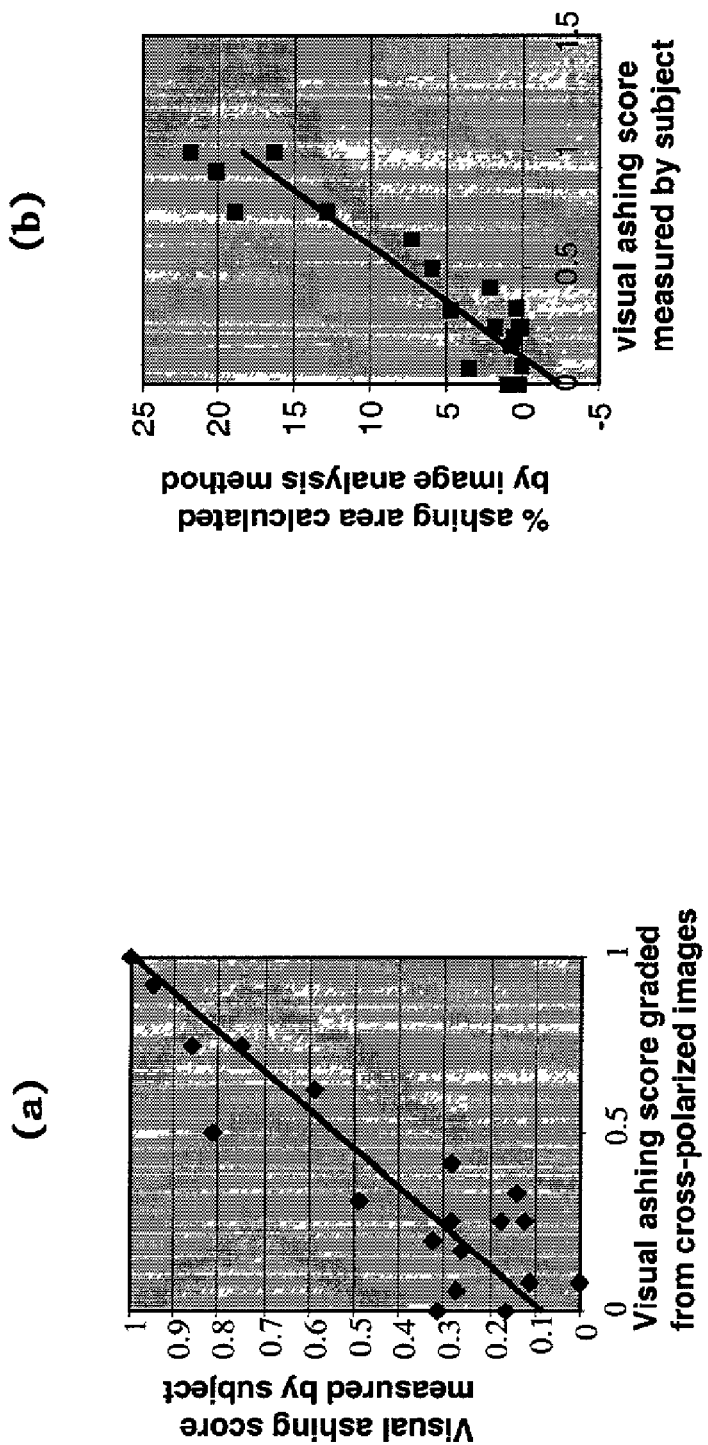
FIG. 2 shows the correlation between visual ash score measured by test subjects; visual ash score compared to score measured from x-polarized images; and visual ash score compared to actually calculated analysis results.

Correlations among visual ash score, visual ash score from cross-polarized pictures, and analysis results are shown in FIG. 2. It can be seen that good correlation exists between visual grade from cross-polarized images and visual grade. Images obtained using the Charm View System have a few advantages over direct visual evaluation. It is less light source and environment dependent. It is also easier to record standard images corresponding to each ash grade. These standard images can provide guidance for visual training of clinical or consumer panels.

Good correlation is observed between visual grades and image analysis results. A great benefit of this method is that uneven pigmentation and hair do not affect the analysis results.

The invention claimed is:

1. A process for measuring skin ashing comprising:
   (a) selecting a desired area of skin to be tested for skin ashing;
   (b) acquiring an image of the desired area with an image capturing device using a x-polarization technique to acquire said image; and
   (c) analyzing said acquired image to determine ashing; wherein the image of step (c) is analyzed by:
      (i) acguiring an original image as described in Step (b);
      (ii) obtaining a light distributing image from the original image;
      (iii) storing the difference between the light distribution image and original image as a new image and;
      (iv) defining a fixed threshold of intensity unit over a baseline intensity to said image and marking areas meeting said threshold in white to define ashing.

2. A process according to claim 1, wherein the desired area is 0.5 to 100 cm$^2$.

3. A process according to claim 1, wherein the image capturing device is a camera.

4. A process according to claim 1, wherein the acquired image is a digital image.

5. A process according to claim 1, wherein said cross-polarized image is acquired at magnification of 1 to 100 times.

6. A process according to claim 1, wherein said light distribution image is obtained by fitting the original image to a parabola in two dimension.

7. A process according to claim 1, wherein said baseline intensity is the average intensity over the image.

8. A process according to claim 1, wherein said fixed threshold is 2 to 100 intensity units over the baseline intensity.

9. A process according to claim 8, wherein said fixed threshold is 5 to 50 intensity units over the baseline.

10. A process according to claim 1, wherein the marked areas at or above threshold define total % ashing.

* * * * *